US011779234B2

(12) United States Patent
Harjes et al.

(10) Patent No.: US 11,779,234 B2
(45) Date of Patent: *Oct. 10, 2023

(54) PRESSURE SENSING VENTRICULAR ASSIST DEVICES AND METHODS OF USE

(71) Applicant: TC1 LLC, St. Paul, MN (US)

(72) Inventors: Daniel I. Harjes, Acton, MA (US); Kathryn B. Frederick, St. Paul, MN (US); Eric Lee, St. Paul, MN (US)

(73) Assignee: TC1 LLC, St. Paul, MN (US)

( * ) Notice: Subject to any disclaimer, the term of this patent is extended or adjusted under 35 U.S.C. 154(b) by 399 days.

This patent is subject to a terminal disclaimer.

(21) Appl. No.: 17/028,687

(22) Filed: Sep. 22, 2020

(65) Prior Publication Data

US 2021/0001025 A1 Jan. 7, 2021

Related U.S. Application Data

(63) Continuation of application No. 15/939,105, filed on Mar. 28, 2018, now Pat. No. 10,835,654.
(Continued)

(51) Int. Cl.
*A61B 5/029* (2006.01)
*A61B 5/00* (2006.01)
(Continued)

(52) U.S. Cl.
CPC ............ *A61B 5/029* (2013.01); *A61B 5/0031* (2013.01); *A61M 60/148* (2021.01);
(Continued)

(58) Field of Classification Search
CPC ... A61M 1/1086; A61M 1/122; A61B 5/0031; A61B 5/029
See application file for complete search history.

(56) References Cited

U.S. PATENT DOCUMENTS 3,911,897 A 10/1975 Leachman
5,139,517 A 8/1992 Corral
(Continued)

FOREIGN PATENT DOCUMENTS

EP 2570143 3/2013
EP 3213781 9/2017
(Continued)

OTHER PUBLICATIONS

Bedi et al., "Ventricular Arrhythmias During Left Ventricular Assist Device Support", Am J Cardiol., vol. 99, Issue 8, 2007, pp. 1151-1153.
(Continued)

*Primary Examiner* — Joseph M Dietrich
(74) *Attorney, Agent, or Firm* — Kilpatrick Townsend & Stockton LLP

(57) ABSTRACT

The invention generally relates to heart pump systems. In some embodiments, a pressure sensor is provided with a heart pump, either at the inflow or the outflow of the blood pump. The heart pump may further include a flow estimator based on a rotor drive current signal delivered to the rotor. Based on the rotor drive current signal, a differential pressure across the pump may be calculated. The differential pressure in combination with the pressure measurements from the pressure sensor may be used to calculate pressure on the opposite side of the pump from the pressure sensor. In some embodiments, the pressure sensor is located at the outflow of the pump and the pump is coupled with the left ventricle. The differential pressure and pressure measurement may be used to calculate a left ventricular pressure waveform of the patient. With such a measurement, other physiological parameters may be derived.

20 Claims, 7 Drawing Sheets

Related U.S. Application Data

(60) Provisional application No. 62/478,492, filed on Mar. 29, 2017.

(51) Int. Cl.
| | |
|---|---|
| *A61M 60/148* | (2021.01) |
| *A61M 60/88* | (2021.01) |
| *A61M 60/546* | (2021.01) |
| *A61M 60/422* | (2021.01) |
| *A61M 60/237* | (2021.01) |
| *A61M 60/178* | (2021.01) |
| *A61M 60/221* | (2021.01) |
| *A61M 60/232* | (2021.01) |
| *A61M 60/531* | (2021.01) |
| *A61B 5/024* | (2006.01) |
| *A61M 60/419* | (2021.01) |

(52) U.S. Cl.
CPC ........ *A61M 60/178* (2021.01); *A61M 60/221* (2021.01); *A61M 60/232* (2021.01); *A61M 60/237* (2021.01); *A61M 60/422* (2021.01); *A61M 60/531* (2021.01); *A61M 60/546* (2021.01); *A61M 60/88* (2021.01); *A61B 5/02405* (2013.01); *A61M 60/419* (2021.01); *A61M 2205/3334* (2013.01); *A61M 2205/3507* (2013.01); *A61M 2210/125* (2013.01)

(56) References Cited

U.S. PATENT DOCUMENTS

| | | |
|---|---|---|
| 5,318,592 A | 6/1994 | Schaldach |
| 5,503,615 A | 4/1996 | Goldstein |
| 6,066,086 A | 5/2000 | Antaki et al. |
| 6,111,520 A | 8/2000 | Allen et al. |
| 6,176,822 B1 | 1/2001 | Nix et al. |
| 6,278,379 B1 | 8/2001 | Allen et al. |
| 6,585,635 B1 | 7/2003 | Aldrich |
| 6,634,224 B1 | 10/2003 | Schoeb et al. |
| 6,643,420 B2 | 11/2003 | Han et al. |
| 6,772,011 B2 | 8/2004 | Dolgin et al. |
| 6,855,115 B2 | 2/2005 | Fonseca et al. |
| 6,984,201 B2 | 1/2006 | Khaghani et al. |
| 7,029,433 B2 | 4/2006 | Chang |
| 7,245,117 B1 | 7/2007 | Joy et al. |
| 7,320,706 B2 | 1/2008 | Al-Najjar |
| 7,439,723 B2 | 10/2008 | Allen et al. |
| 7,498,799 B2 | 3/2009 | Allen et al. |
| 7,520,850 B2 | 4/2009 | Brockway |
| 7,550,978 B2 | 6/2009 | Joy et al. |
| 7,679,355 B2 | 3/2010 | Allen et al. |
| 7,839,153 B2 | 11/2010 | Joy et al. |
| 7,853,325 B2 | 12/2010 | Dabney et al. |
| 7,862,501 B2 | 1/2011 | Woodard |
| 7,945,333 B2 | 5/2011 | Jacobson |
| 7,963,905 B2 | 6/2011 | Salmonsen et al. |
| 7,988,728 B2 | 8/2011 | Ayre |
| 7,998,054 B2 | 8/2011 | Bolling |
| 8,145,324 B1 | 3/2012 | Stevenson et al. |
| 8,177,838 B2 | 5/2012 | Vodermayer et al. |
| 8,180,448 B2 | 5/2012 | Stevenson et al. |
| 8,224,462 B2 | 7/2012 | Westlund et al. |
| 8,246,530 B2 | 8/2012 | Sullivan |
| 8,295,939 B2 | 10/2012 | Jacobson |
| 8,364,283 B2 | 1/2013 | Halperin et al. |
| 8,506,471 B2 | 8/2013 | Bourque |
| 8,543,205 B2 | 9/2013 | Ostroff |
| 8,608,636 B2 | 12/2013 | Choi et al. |
| 8,657,733 B2 | 2/2014 | Ayre et al. |
| 8,682,431 B2 | 3/2014 | Callaway et al. |
| 8,712,544 B2 | 4/2014 | Dabney et al. |
| 8,771,165 B2 | 7/2014 | Choi et al. |
| 8,794,989 B2 | 8/2014 | Kearsley et al. |
| 8,852,099 B2 | 10/2014 | Von Arx et al. |
| 8,864,644 B2 | 10/2014 | Yomtov |
| 8,894,561 B2 | 11/2014 | Callaway et al. |
| 8,897,887 B2 | 11/2014 | Halperin et al. |
| 9,039,595 B2 | 5/2015 | Ayre et al. |
| 9,090,271 B2 | 7/2015 | Bartonek |
| 9,387,284 B2 | 7/2016 | Heilman et al. |
| 9,433,714 B2 | 9/2016 | Voskoboynikov et al. |
| 9,579,432 B2 | 2/2017 | Tamez et al. |
| 9,579,435 B2 | 2/2017 | Yomtov |
| 9,592,327 B2 | 3/2017 | Wariar et al. |
| 9,833,552 B2 | 12/2017 | Yomtov |
| 10,780,209 B2 | 9/2020 | Harjes et al. |
| 2005/0071001 A1 | 3/2005 | Jarvik |
| 2007/0088397 A1 | 4/2007 | Jacobson |
| 2008/0281146 A1 | 11/2008 | Morello |
| 2010/0241223 A1 | 9/2010 | Lee et al. |
| 2011/0178361 A1 | 7/2011 | Yomtov |
| 2011/0270331 A1 | 11/2011 | Peters et al. |
| 2012/0253207 A1 | 10/2012 | Sarkar et al. |
| 2012/0271367 A1 | 10/2012 | Qu et al. |
| 2013/0072846 A1 | 3/2013 | Heide et al. |
| 2014/0012067 A1 | 1/2014 | Poirier |
| 2014/0046120 A1 | 2/2014 | Choi et al. |
| 2014/0058190 A1 | 2/2014 | Gohean et al. |
| 2014/0188148 A1 | 7/2014 | Le Blanc et al. |
| 2015/0057488 A1 | 2/2015 | Yomtov |
| 2015/0073203 A1 | 3/2015 | Wariar et al. |
| 2015/0148587 A1 | 5/2015 | Bourque |
| 2015/0151032 A1 | 6/2015 | Voskoboynikov et al. |
| 2015/0174307 A1 | 6/2015 | Eckman et al. |
| 2015/0290374 A1 | 10/2015 | Bourque et al. |
| 2015/0328466 A1 | 11/2015 | Peters et al. |
| 2016/0058929 A1 | 3/2016 | Medvedev et al. |
| 2016/0058930 A1 | 3/2016 | Medvedev et al. |
| 2016/0101230 A1 | 4/2016 | Ochsner et al. |
| 2016/0193397 A9 | 7/2016 | Aber et al. |
| 2016/0228628 A1 | 8/2016 | Medvedev et al. |
| 2016/0263299 A1 | 9/2016 | Xu et al. |
| 2017/0021070 A1 | 1/2017 | Petersen |
| 2017/0080138 A1 | 3/2017 | Yomtov |
| 2017/0128646 A1* | 5/2017 | Karch ............... A61M 60/148 |
| 2018/0050348 A1 | 2/2018 | Whitney |
| 2018/0078689 A1 | 3/2018 | Yomtov |
| 2018/0140760 A1 | 5/2018 | Cotter |
| 2018/0280599 A1 | 10/2018 | Harjes et al. |
| 2018/0280600 A1 | 10/2018 | Harjes et al. |

FOREIGN PATENT DOCUMENTS

| | | |
|---|---|---|
| WO | 2007089500 | 8/2007 |
| WO | 2011123789 | 10/2011 |
| WO | 2016001284 | 1/2016 |
| WO | 2016137743 | 9/2016 |
| WO | 2017117185 | 7/2017 |
| WO | 2017117215 | 7/2017 |
| WO | 2017139113 | 8/2017 |

OTHER PUBLICATIONS

Brisco et al., "The Incidence, Risk, and Consequences of Atrial Arrhythmias In Patients With Continuous-flow Left Ventricular Assist Devices", J Card Surg, vol. 29, Issue 4, 2014, pp. 572-580.

Clark et al., "Hemodynamic Effects of An Irregular Sequence of Ventricular Cycle Lengths During Atrial Fibrillation", Journal of the American College of Cardiology, vol. 30, Issue 4, 2007, pp. 1039-1045.

Enriquez et al., "Clinical Impact of Atrial Fibrillation In Patients With The Heartmate Ii Left Ventricular Assist Device", Journal of the American College of Cardiology, vol. 64, Issue 18, 2014, pp. 1883-1890.

Hayward et al., "Effect of Alteration In Pump Speed on Pump Output and Left Ventricular Filling With Continuous-flow Left Ventricular Assist Device", ASAIO Journal. vol. 57, issue 6, 2011, pp. 495-500.

Maeda et al., "Predictive Control by Physical Activity Rate of a Total Artificial Heart During Exercise", Transactions of the American Society of Artificial Internal Organs, vol. 34, 1988, pp. 480-484.

(56) References Cited

OTHER PUBLICATIONS

Maury et al., "First Experience of Percutaneous Radio-frequency Ablation for Atrial Flutter and Atrial Fibrillation In A Patient With Heartmate Ii Left Ventricular Assist Device", Journal of Interventional Cardiac Electrophysiology, vol. 29, Issue 1, 2010, pp. 63-67.

Oswald et al., "Implantable Defibrillator Therapy for Ventricular Tachyarrhythmia In Left Ventricular Assist Device Patients", Eur J Heart Fail., vol. 12, Issue 6, 2010, pp. 593-599.

Oz et al., "Malignant Ventricular Arrhythmias Are Well Tolerated In Patients Receiving Long-term Left Ventricular Assist Devices", Journal of the American College of Cardiology, vol. 24, Issue 7, 1994, pp. 1688-1691.

Raasch et al., "Epidemiology, Management, and Outcomes of Sustained Ventricular Arrhythmias After Continuous-flow Left Ventricular Assist Device Implantation", Am Heart J., vol. 164, Issue 3, 2012, pp. 373-378.

Ziv et al., "Effects of Left Ventricular Assist Device Therapy on Ventricular Arrhythmias", Journal of the American College of Cardiology, vol. 45, Issue 9, 2005, pp. 1428-1434.

\* cited by examiner

PRESSURE SENSING VENTRICULAR ASSIST DEVICES AND METHODS OF USE

CROSS-REFERENCE TO RELATED APPLICATIONS

The present application is a Continuation of U.S. patent application Ser. No. 15/939,105 filed Mar. 28, 2018 (Allowed); which claims the benefit of U.S. Provisional Appln No. 62/478,492 filed Mar. 29, 2017; the full disclosures which are incorporated herein by reference in their entirety for all purposes.

BACKGROUND

Heart disease is a growing epidemic in the United States that can lead to heart failure. Heart failure is characterized as a progressive, downward spiral in heart function. In particular, cardiac injury can cause cardiac dysfunction, which results in reduced cardiac output. Some results of reduced cardiac output are endothelial dysfunction, neurohormonal activation, renal impairment, and vasoconstriction. These results can lead to fluid retention and increased systemic vascular resistance. An increase in systemic vascular resistance can create increased cardiac load which can cause further cardiac dysfunction. Thus a cycle of further cardiac dysfunction can be established.

Although there are various treatments proposed and being developed for treating heart failure, such systems are generally limited to the hospital setting or at least require the patient to be very limited in mobility if not completely confined to a bed. Some patients have turned to implantable blood pumps, such as ventricular assist devices (VAD), for assisting in heart pumping or effectively replacing the natural heart's function. Most patients recover in a way where they improve in functional class, however, only a small percentage of patients exhibit restoration to the point of explant and the number of hearts available for heart transplant is insufficient to meet demand. As such, the blood pumps are typically required for life. Accordingly, it may be advantageous to further improve blood pump devices, systems, and methods to coordinate pumping functions and to monitor patient physiological parameters during the long term implantation (e.g., destination therapy or bridge to transplantation) of the implantable blood pump so there is continuing need to improve pumps and LVAD therapy. Here, there is need for pressure reading to better provide therapy and/or actively adjust pump parameters based on the patient. For example, a patient may recover over time and the pump can be adjusted accordingly. Optionally, the pump may be adjusted for patient exercise or activity.

BRIEF SUMMARY

The present invention generally relates to heart pump systems and methods of use. In some embodiments, a method of hemodynamic monitoring is provided for a patient having an implanted heart pump. In further embodiments, a heart pump is provided that may monitor physiological parameters of the patient and may adjust pumping (e.g., speed, mode, flow rate, or the like) in response to the monitored parameters and/or may report the monitored parameters to a physician.

Many rotary blood pumps may estimate flow through the heart pump, for example, by sensing the electrical current required to drive the rotor at a particular speed. This information may be beneficial for clinicians for determining changes in pump performance associated with a physiological state (e.g., suction detection, patient hypertension, etc.). However, the pump flow rate information alone may be of limited value in diagnosing the patient's hemodynamic state and/or determining if the heart pump is providing adequate flow support (or too much or too little). Patients may have dramatically different cardiac output needs and these needs may change depending on a number of factors (e.g., rest, exercise, stress, left ventricular recovery, time of day, etc.).

Cardiovascular pressure measurements can provide a host of valuable data that is directly applicable for determining a patient's hemodynamic state and optimizing blood pump settings. For example, a physician may want to specifically tailor a pump flow rate or pump speed depending on patient characteristics. To determine the appropriate flow rate or speed, the physician may benefit from additional information, such as the left ventricular pressure, pulmonary arterial pressure, etc. There are a number of potential sensor devices and locations applicable to the present invention. In particular, real time high speed (e.g., ~50 Hz) pressure measurements of the left ventricle and the aorta may be particularly valuable for left ventricular assist device (LVAD) applications. With such measurements, other clinical parameters may be derived, such as systolic arterial pressure, diastolic arterial pressure, mean arterial pressure, systemic resistance estimation, aortic compliance estimation, end diastolic pressure (LV filling pressure), end systolic pressure, LV contractility estimation, degree of aortic valve opening, stroke volume and/or cardiac output estimation. Additionally, pressure measurements may be used to increase the accuracy of flow rate estimations based on drive current, similar to the concepts described in U.S. patent application Ser. No. 15/212,721 (now issued as U.S. Pat. No. 10,722,630), the contents of which are incorporated herein by reference in their entirety.

In some embodiments of the present invention, a method for hemodynamic monitoring of a patient may be provided. The method may include receiving a differential pressure across the heart pump having an inflow and an outflow. A pressure measurement may be received from a pressure sensor positioned in the inflow or the outflow of the heart pump. A data waveform of interest may be calculated from the differential pressure across the heart pump and the pressure measurement from the pressure sensor positioned in the inflow or the outflow of the heart pump.

In some embodiments, the calculated data waveform of interest may be outputted (e.g., to a patient or a clinician). In some embodiments, a pumping of the heart pump may be adjusted in response to the calculated data waveform. In some embodiments, the pressure sensor is positioned in the outflow of the heart pump. The differential pressure across the heart pump may be calculated based on a rotor drive current associated with the heart pump. In some embodiments, the data waveform of interest comprises a left ventricular pressure waveform and the left ventricular pressure waveform may be calculated by subtracting the differential pressure from the pressure measurement.

In further aspects of the present invention, a blood pump system may be provided. The system may include a blood pump comprising an inlet and an outlet. A pressure sensor may be provided that is coupled with the inlet or the outlet of the blood pump. A controller operably coupled with the blood pump and the pressure sensor may be configured to receive a differential pressure across the blood pump and a pressure measurement from the pressure sensor. The controller may be configured to calculate a data waveform of interest from the differential pressure across the blood pump and the pressure measurement from the pressure sensor.

In some embodiments, the controller is configured to output the calculated data waveform. Optionally, the controller is configured to adjust a pumping of the heart pump in response to the calculated data waveform. In some embodiments, the sensor is positioned on the outflow of the blood pump. In some embodiments, the controller calculates the differential pressure across the blood pump based on a rotor driver current associated with the blood pump. In certain embodiments, the data waveform of interest comprises a left ventricular pressure waveform and the left ventricular pressure waveform may be calculated by subtracting the differential pressure from the pressure measurement.

Embodiments of the disclosure covered by this patent are defined by the claims below, not this summary. This summary is a high-level overview of various aspects of the invention and introduces some of the concepts that are further described in the Detailed Description section below. This summary is not intended to identify key or essential features of the claimed subject matter, nor is it intended to be used in isolation to determine the scope of the claimed subject matter. The subject matter should be understood by reference to appropriate portions of the entire specification of this patent, any or all drawings, and each claim.

The disclosure will be better understood upon reading the following description and examining the figures which accompany it. These figures are provided by way of illustration only and are in no way limiting on the invention.

BRIEF DESCRIPTION OF THE DRAWINGS

Further details, aspects, and embodiments of the invention will be described by way of example only and with reference to the drawings. In the drawings, like reference numbers are used to identify like or functionally similar elements. Elements in the figures are illustrated for simplicity and clarity and have not necessarily been drawn to scale.

DETAILED DESCRIPTION

Figure 1:
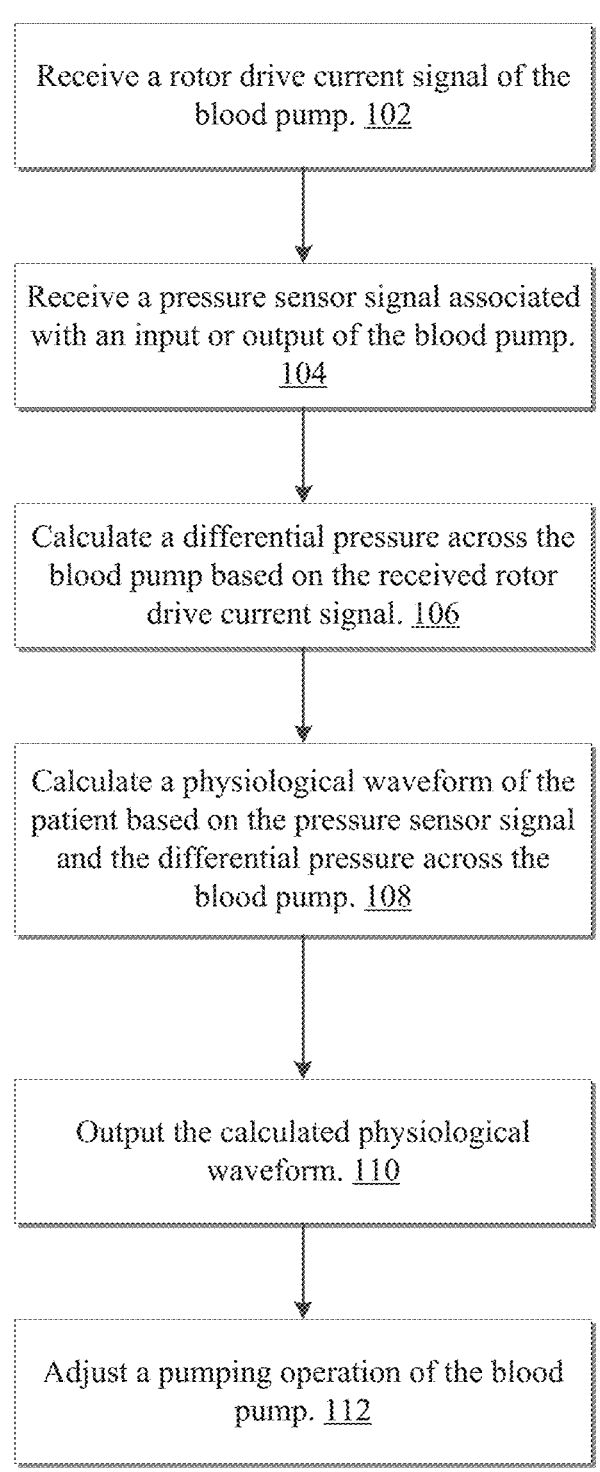
FIG. 1 illustrates an exemplary method according to some embodiments.

FIG. 1 illustrates an exemplary method 100 for estimating physiological waveforms of interest of a patient with a blood pump according to some embodiments. The method 100 may include receiving a rotor drive current signal of the blood pump 102. A pressure sensor signal that is associated with an input or an output of the blood pump may also be received 104. A differential pressure across the blood pump may be calculated based on the received rotor drive current signal 106. A physiological waveform of the patient may be calculated based on the received pressure sensor signal and the differential pressure across the blood pump 108. Thereafter, the calculated physiological waveform may be outputted 110. Additionally, a pumping operation of the blood pump may be adjusted in response to the calculated physiological waveform 112.

Method 100 may be used to estimate the left ventricular pressure waveform. Additionally, the aortic pressure waveform may be calculated separate from or in addition to the left ventricular pressure waveform. With such measurements, other clinical parameters may be derived, such as: systolic arterial pressure, diastolic arterial pressure, mean arterial pressure, systemic resistance estimation, aortic compliance estimation, end diastolic pressure (LV filling pressure), end systolic pressure, LV contractility estimation, degree of aortic valve opening, stroke volume and cardiac output estimation. While generally discussed as estimating parameters associated with the left ventricle, it should be understood that the method 100 is applicable to measuring parameters associated with other chambers of the heart (e.g., right ventricle, left atrium, etc.), depending on where the heart pump is implanted.

Figure 2:
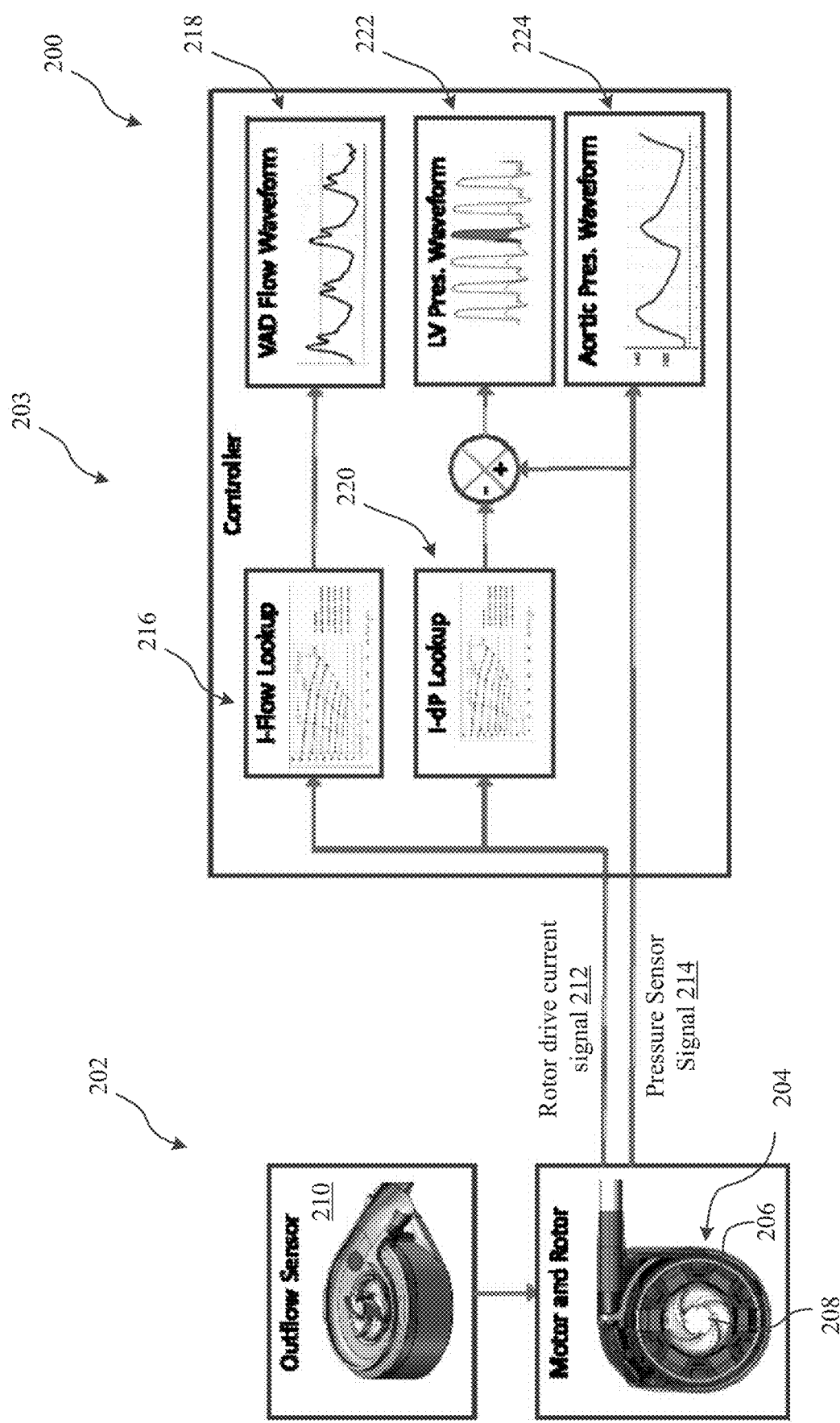
FIG. 2 illustrates an exemplary system according to some embodiments.

FIG. 2 illustrates an exemplary heart pump system 200 according to some embodiments that may be configured to carry out method 100 of FIG. 1 to estimate left ventricular pressure waveform, VAD flow waveform, and aortic pressure waveform. Heart pump system 200 comprises a left ventricular heart pump 202 and a controller 203. In some embodiments, the pump 202 can be configured similar to an LVAD described in U.S. Patent Publication 2015/0290374; U.S. Patent Publication 2014/0188148; U.S. Pat. Nos. 9,091,271; 8,794,989, 8,682,431; and/or U.S. Pat. No. 8,894,561, the contents of which are incorporated herein by reference in their entirety. The heart pump 202 includes a housing 204. Housing 204 encloses a motor 206 and rotor 208. Housing 204 may also house a pressure sensor 210. Optionally, pressure sensor 210 may be wired directly to the motor 206. While pressure sensor 210 is illustrated as positioned in the outflow of heart pump 202, in other embodiments, pressure sensor 210 may be positioned in the inflow of heart pump 202.

Figure 3:
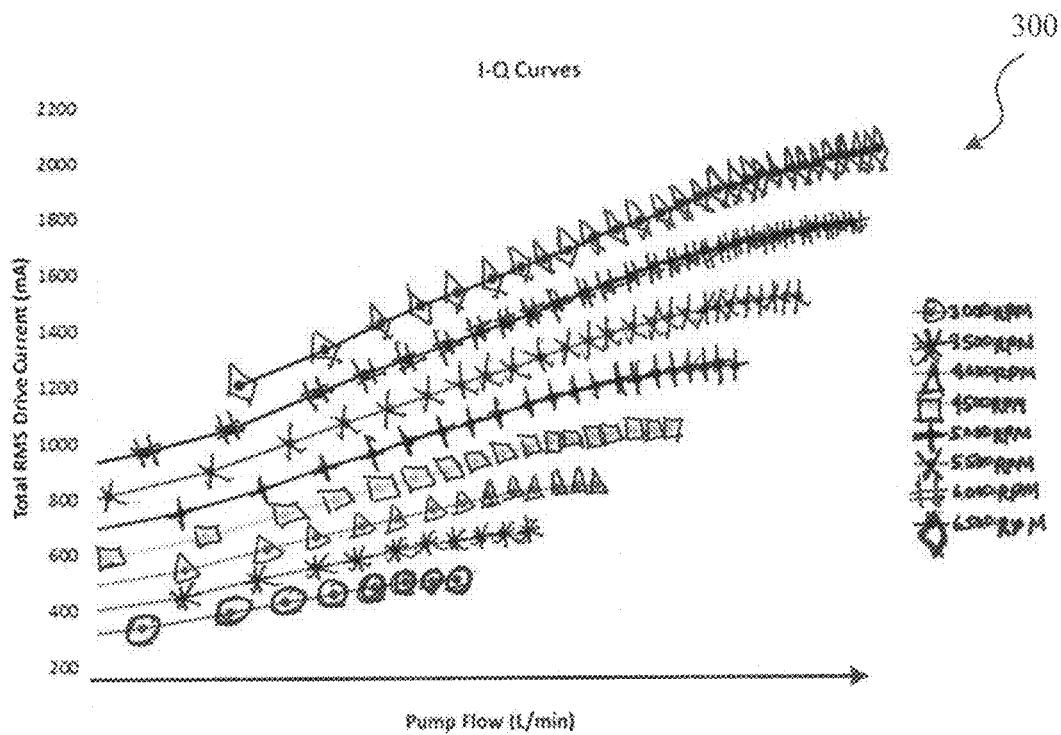
FIG. 3 illustrates an exemplary I-Q curve lookup table.
Figure 4:
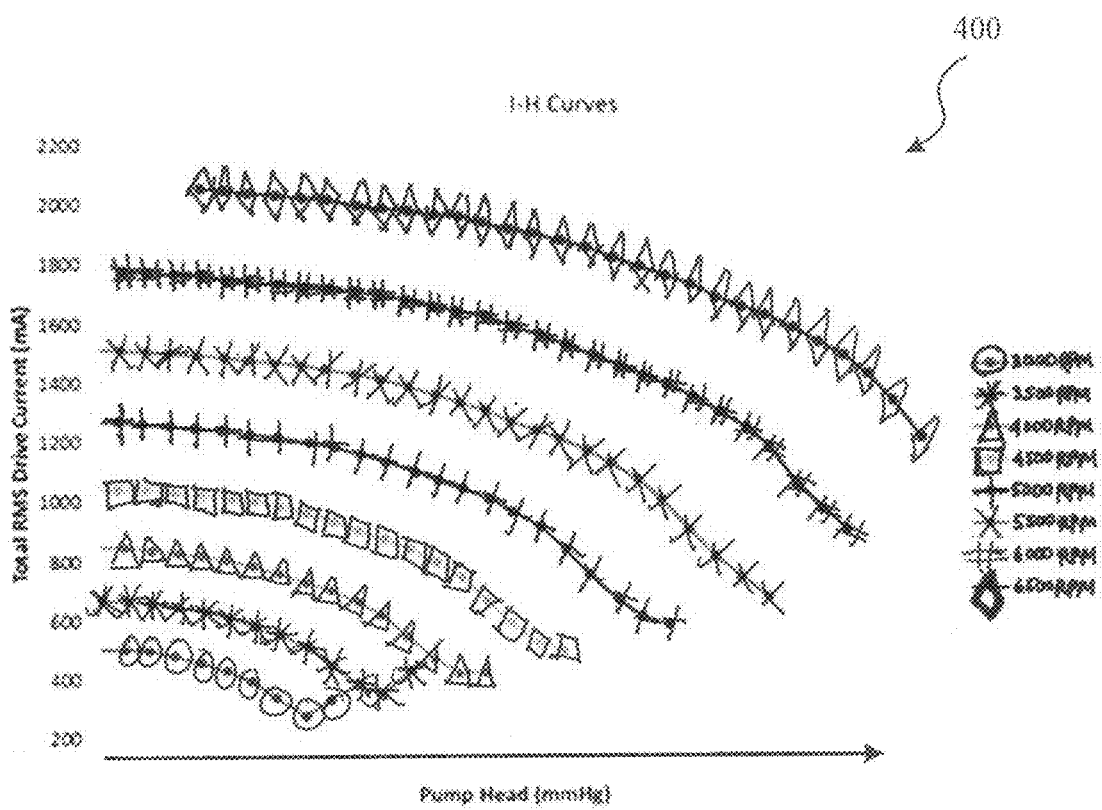
FIG. 4 illustrates an exemplary I-H curve lookup table.

Controller 203 may be an on-board controller of heart pump 202 or may be an external controller (e.g., coupled to the heart pump 202 through a percutaneous cable, wirelessly, or the like). Controller 203 may be operably coupled with the motor 206 and the pressure sensor 210 and may receive a rotor drive current signal 212 and a pressure sensor signal 214 from the heart pump 202. With the received rotor drive current signal 212, the controller 203 may estimate a pump flow by accessing a lookup table 216 associating the received current signal (I) to pump flow rate (Q). FIG. 3 illustrates an exemplary I-Q curve lookup table 300. In some embodiments, rotor rpm and/or hematocrit may be used, in addition with or alternatively to, current signal to provide an accurate flow rate calculation. By continuously estimating pump flow, the controller 203 may estimate a VAD flow waveform 218. Additionally, with the received rotor drive current signal 212, the controller 203 may also estimate a differential pressure across the pump by accessing a lookup table 220 associating the received current signal (I) to differential pressure across the pump (dP). In some embodiments, the rotor rpm and/or hematocrit may be used, in addition with or alternatively to, rotor current signal to provide an accurate differential pressure measurement. In some embodiments which use magnetic levitation rotors, hall effect sensor signals may be used to provide rotor positional information which may also be a pressure dependent phenomenon. Accordingly, rotor positional information and/or hall effect sensor signals may be used in addition, or alternatively, to rotor current, rotor rpm, and/or hematocrit to provide accurate differential pressure measurements. U.S. patent application Ser. No. 15/214,099 describes systems and methods that use hall effect sensors to provide rotor positional information, the contents of which are incorporated herein by reference in their entirety, which may be used with embodiments of the present disclosure to provide differential pressure measurements, ventricular pressure measurements, and proxies thereto. In some embodiments, both rotor current signal and positional information may be used to provide accurate differential pressure measurements. For example, rotor current signal may be more accurate for a first range, and positional information may be more accurate for a second range. FIG. 4 illustrates an exemplary I-H curve lookup table 400. In some embodiments, heart rate, start of systole, and/or start of diastole may be identified using the methods and systems described in U.S. patent application Ser. No. 15/041,716, the contents of which are incorporated herein by reference in their entirety, and the pump speed may be modulated accordingly based on one or more of those identified parameters. The controller 203 may calculate the left ventricular pressure waveform 222 by subtracting the estimated differential pressures from the received pressure sensor signal 214. Additionally, the controller 203 may associate the pressure sensor signal 214 with an aortic pressure waveform 224 when the outflow of the heart pump 202 is coupled with the aorta of the patient. The controller 203 may output the VAD flow waveform 218, the left ventricular pressure waveform 222, and/or the aortic pressure waveform 224 to a user or clinician. As mentioned above, with such measurements, other clinical parameters may be derived, such as: systolic arterial pressure, diastolic arterial pressure, mean arterial pressure, systemic resistance estimation, aortic compliance estimation, end diastolic pressure (LV filling pressure), end systolic pressure, LV contractility estimation, degree of aortic valve opening, stroke volume and cardiac output estimation. Accordingly, these waveforms could be run through subsequent algorithms to calculate added clinical parameters of interest (e.g., cardiac output, heart rate, etc.).

The controller 203 may also be configured to adjust the pumping operation of the pump in response to the estimated VAD flow waveform 218, the left ventricular pressure waveform 222, and/or the aortic pressure waveform 224. For example, in some embodiments, the left ventricular pressure waveform 222 may be associated with a heart rate of a patient, thereby providing patient activity information. The heart rate may be automatically calculated by analyzing the rate of left ventricular pressure change in the estimated left ventricular pressure waveform 222 which can also indicates the start of systole. In some embodiments, a threshold rate of left ventricular pressure change may be used to identify individual heart beats in the calculated left ventricular pressure waveform. With changes in heart rate or activity of a patient, a pumping operation of a heart pump 202 may be increased (during increased heart rate/activity) or decreased (during decreased heart rate/activity) in response. This may be particularly advantageous as separate patient heart rate sensor or activity monitor may not be needed, thereby possibly reducing complexity and power consumption of a system 200.

In addition, a left ventricular contractility estimate may be estimated based on the left ventricular pressure waveform. For example, the contractility estimate may be associated with a gradient of a train of the left ventricular pressure waveform.

The measured pressure may act as a proxy for one or more other clinical parameters, including but not limited to filling pressure, systolic arterial pressure, diastolic arterial pressure, mean arterial pressure, systemic resistance estimation, aortic compliance estimation, end diastolic pressure, end systolic pressure, LV contractility estimation, degree of aortic valve opening, and/or stroke volume and cardiac output estimation. For example, a left ventricular pressure waveform and an aortic pressure waveform may be used to calculate one or more of the above parameters.

While heart pump 202 is generally illustrated as a centrifugal flow heart pump, it should be understood that heart pump 202 may have other configurations. For example, in some embodiments, heart pump 202 may be an axial flow blood pump or a mixed flow blood pump.

Figure 5:
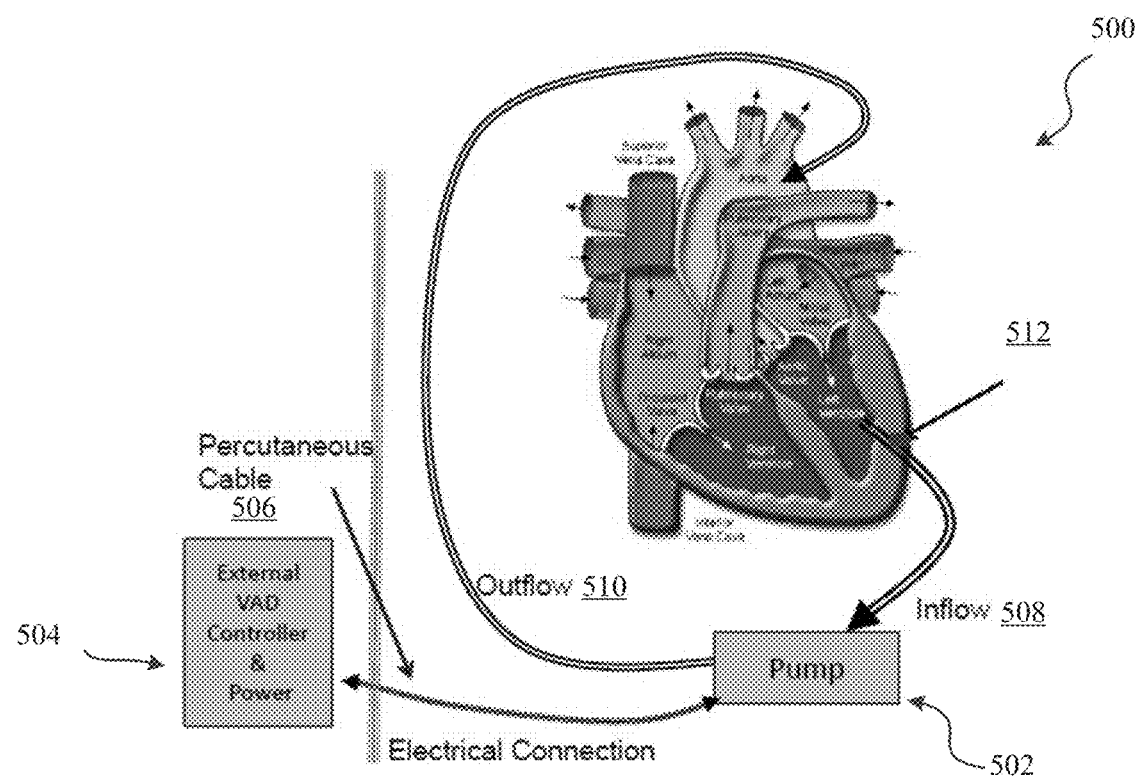
FIG. 5 illustrates an exemplary heart pump system according to some embodiments.

Pressure sensor may be interrogated at a fast rate (~50 Hz) in combination with rotor torque measurements to provide real-time waveforms for LV pressure, VAD flow, and aortic pressure. Further, as mentioned above pressure sensor 210 may be integrated in the inflow of heart pump 202. For example, FIG. 5 illustrates an exemplary heart pump system 500 that includes a pump 502 and an external controller 504. The pump 502 and the external controller 504 may be operably connected to one another (e.g., by a percutaneous cable 506 or the like). The pump 502 may include an inflow 508 coupled to a chamber of the heart and an outflow 510 coupled with an aorta of the patient. The heart pump system 500 may further include a pressure sensor 512 along a portion of the inflow 508 of the heart pump 502. While inflow 508 is illustrated as coupled to the left ventricle, it should be understood that inflow 508 may be coupled to other chambers of the heart, such as the right ventricle or the left atrium. Depending on the implantation location, a pump 502 may be switched to alternative pre-programmed configurations for measuring particular heart parameters (e.g., right ventricular pressure waveforms, left atrium pressure waveforms, associated filling pressures/contractility, etc.).

Alternatively, the pressure sensor 210 may be connected via flying lead (wired). In some embodiments, it may be advantageous to integrate the sensor 210 directly into the pump housing. For example, the sensor 210 could be directly wired to the motor electronics and the sensor 210 itself may be well protected from damage during use. In addition, the volute/outflow is typically less prone to tissue buildup/fouling than the LV or pump inflow. In such embodiments, the sensor 210 may be located anywhere from the volute to the aorta.

Many traditional sensors could be used, including MEMS, strain gauges, piezo-based sensors, capacitive sensors, transonic, ultrasound Doppler, or the like. U.S. Provisional Patent Application No. 62/194,700 and U.S. Provisional Patent Application No. 62/194,608 describe pressure sensor configurations and pressure sensing methods that may be utilized in embodiments of the present disclosure. The contents of each provisional patent application are incorporated herein in their entirety for all purposes.

Figure 10:
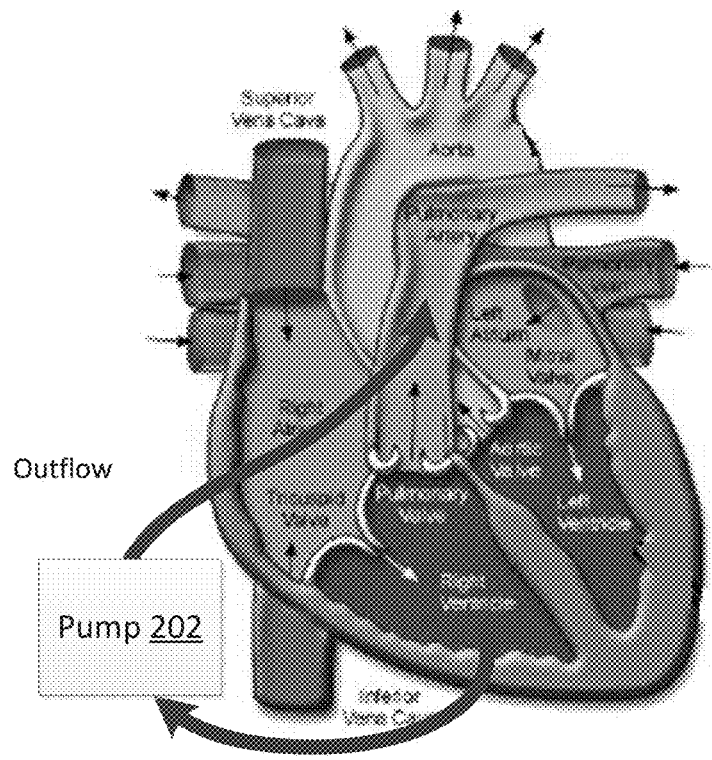
FIG. 10 illustrates an exemplary implantation location of a heart pump according to some embodiments.
Figure 11:
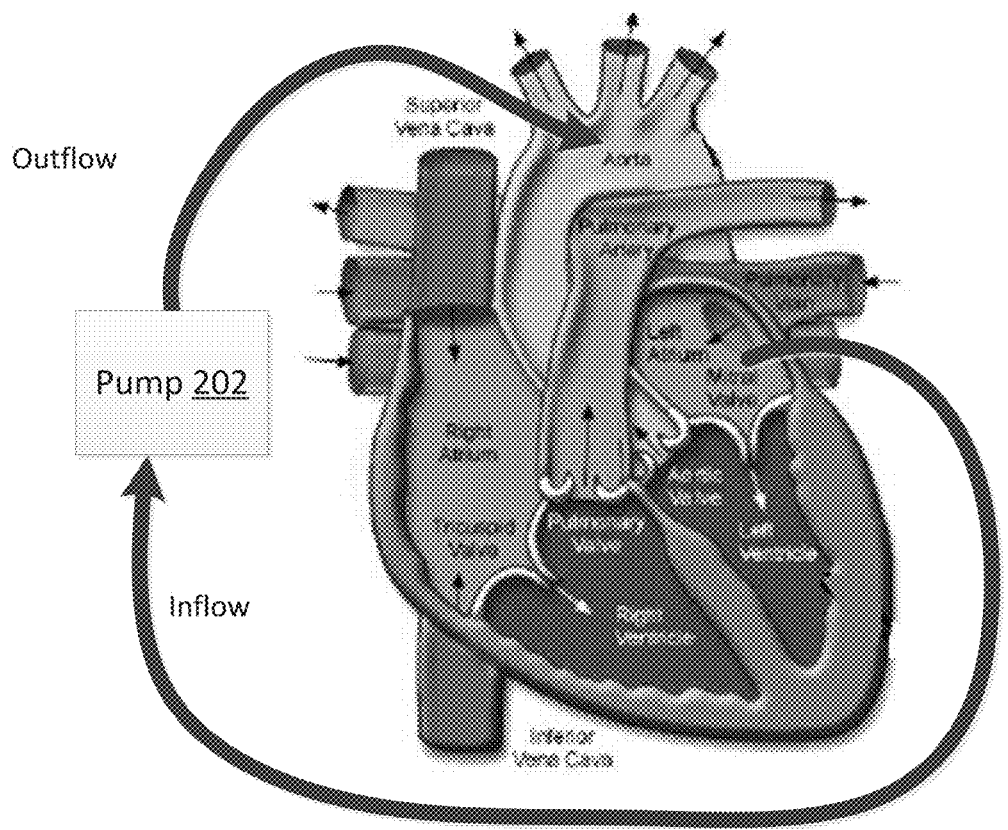
FIG. 11 illustrates another exemplary implantation location of a heart pump according to some embodiments.

Additionally, heart pump 202 is generally described for implantation in the left ventricle and for estimation of left ventricular parameters, but heart pump 202 may also be configured to couple with other portions of the heart. For example, in some embodiments, heart pump 202 may couple with the right ventricle, as illustrated in FIG. 10, or the left atrium, as illustrated in FIG. 11. The controller 203 may be switched to different pre-programmed configurations depending on the implantation location, so that the signal processing output is associated with the correct physiological parameters. For example, if the heart pump 202 is directly cannulated to the right ventricle, it may be programmed to output the right ventricular pressure waveform and/or the pulmonary arterial pressure waveform using similar signal processing described above. Similarly, if the heart pump 202 is directly cannulated to the left atrium, it may be programmed to output the left atrial pressure waveform using similar signal processing described above.

Figure 6:
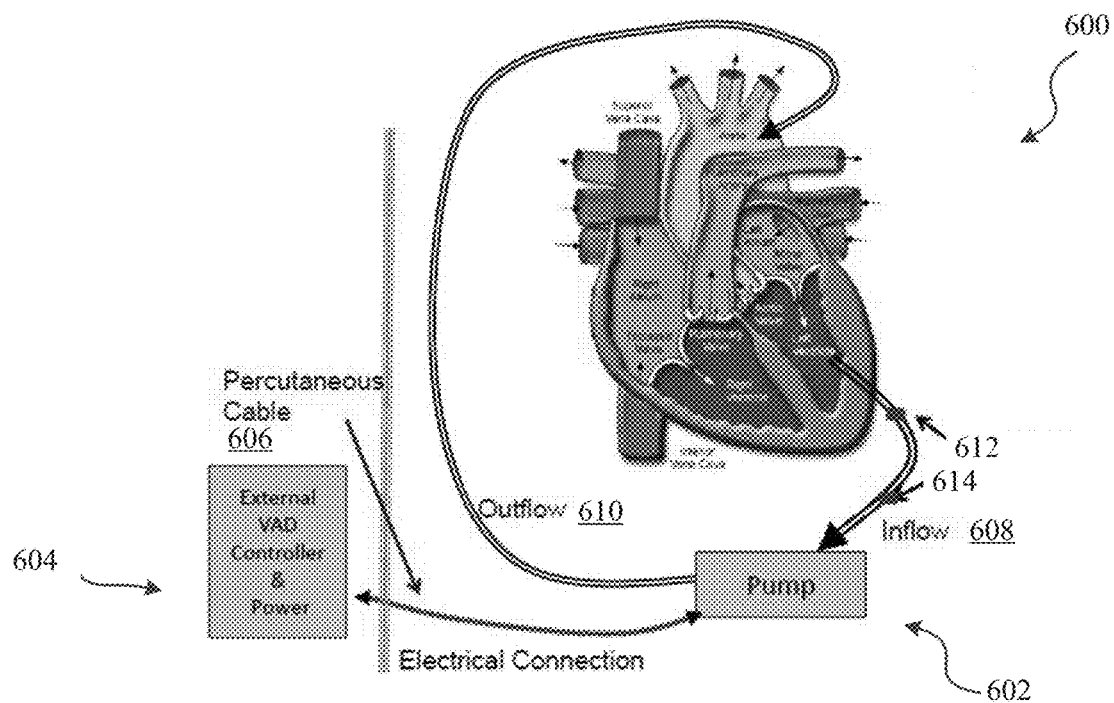
FIG. 6 illustrates another exemplary heart pump system according to some embodiments.

In still further embodiments of the present disclosure, a pressure differential across the pump may be received from a plurality of pressure sensors of the heart pump in the alternative to (or in addition to) computing the pressure differential based on a rotor drive current signal. For example, FIG. 6 illustrates an exemplary heart pump system 600. System 600 includes a pump 602 and an external controller 604. The pump 602 and the external controller 604 may be operably connected to one another (e.g., by a percutaneous cable 606 or the like). The pump 602 may include an inflow 608 coupled to a chamber of the heart (illustrated as the left ventricle, but other chambers may be cannulated by inflow 608) and an outflow 610. The inflow 608 may include an upstream pressure sensor 612 and a downstream pressure 614. The upstream and downstream pressure sensors 612, 614 may provide differential pressure information between the upstream and downstream pressure sensors 612, 614 and may also provide flow information. Further, the two sensors 612, 614 may provide more accurate pressure measurements and may help calibrate measurements to account for sensor drift. In some embodiments, where the inflow has sufficient hydraulic resistance therethrough, the pressure sensors 612, 614 may provide flow information.

Figure 7:
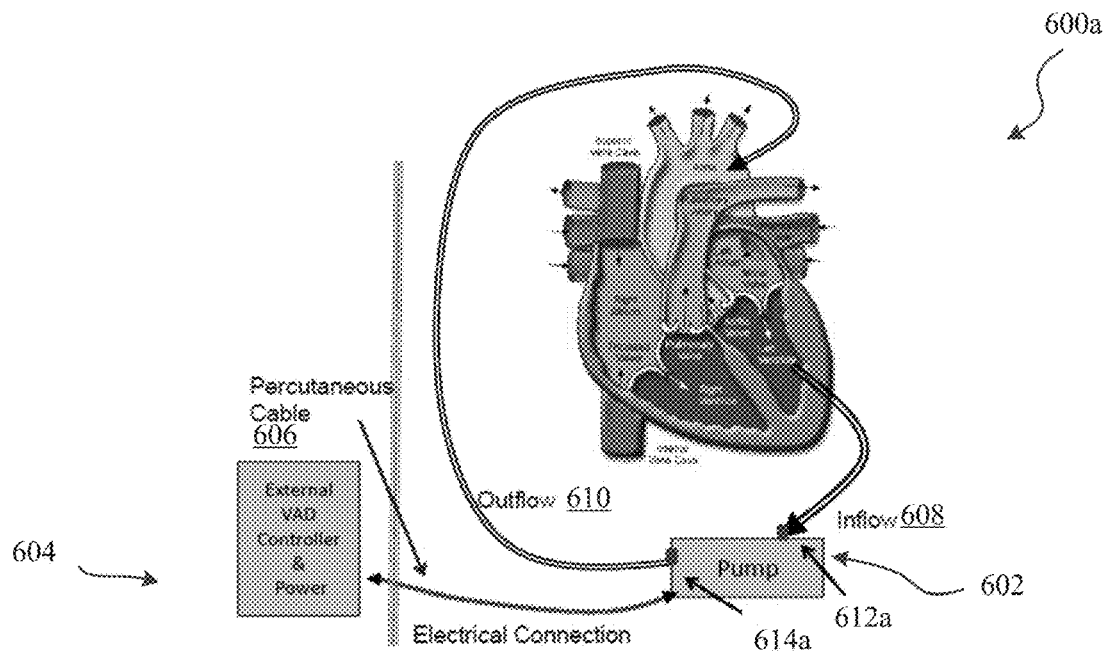
FIG. 7 illustrates another exemplary heart pump system according to some embodiments.

FIG. 7 illustrates another exemplary heart pump system 600a. Heart pump system 600a is similar to system 600 of FIG. 6, except upstream pressure sensor 612a is positioned along the inflow 608 and the downstream pressure sensor 614a is positioned along the outflow 610. The upstream and downstream pressure sensors 612a, 614a may provide differential pressure information between the upstream and downstream pressure sensors 612a, 614a and may also provide flow information. Further, the two sensors 612a, 614a may provide more accurate pressure measurements and may help calibrate measurements to account for sensor drift. In some embodiments, where the fluid conduit between the inflow and outflow has sufficient hydraulic resistance therethrough, the pressure sensors 612a, 614a may provide flow information.

Figure 8:
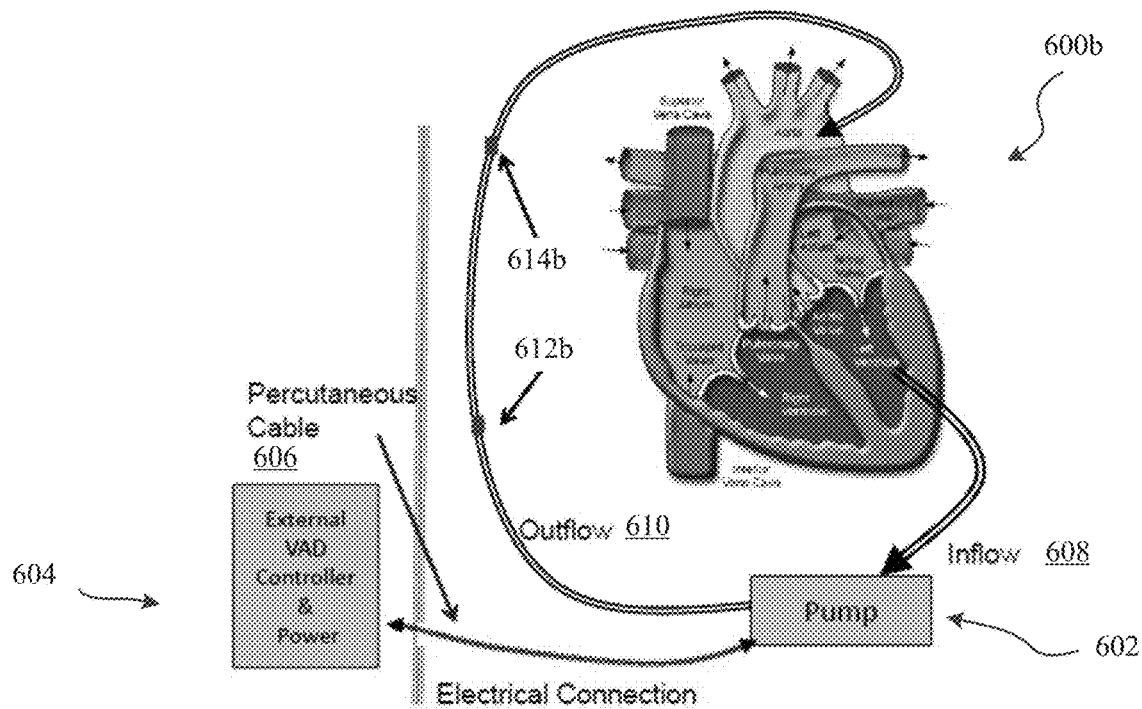
FIG. 8 illustrates another exemplary heart pump system according to some embodiments.

FIG. 8 illustrates another exemplary heart pump system 600b. Heart pump system 600b is similar to system 600 of FIG. 6, except upstream pressure sensor 612b is positioned along the outflow 610 and the downstream pressure sensor 614b is positioned along the outflow 610 downstream from upstream pressure sensor 612b. The upstream and downstream pressure sensors 612b, 614b may provide differential pressure information between the upstream and downstream pressure sensors 612b, 614b and may also provide flow information. Further, the two sensors 612b, 614b may provide more accurate pressure measurements and may help calibrate measurements to account for sensor drift. In some embodiments, where the outflow has sufficient hydraulic resistance therethrough, the pressure sensors 612b, 614b may provide flow information.

Figure 9:
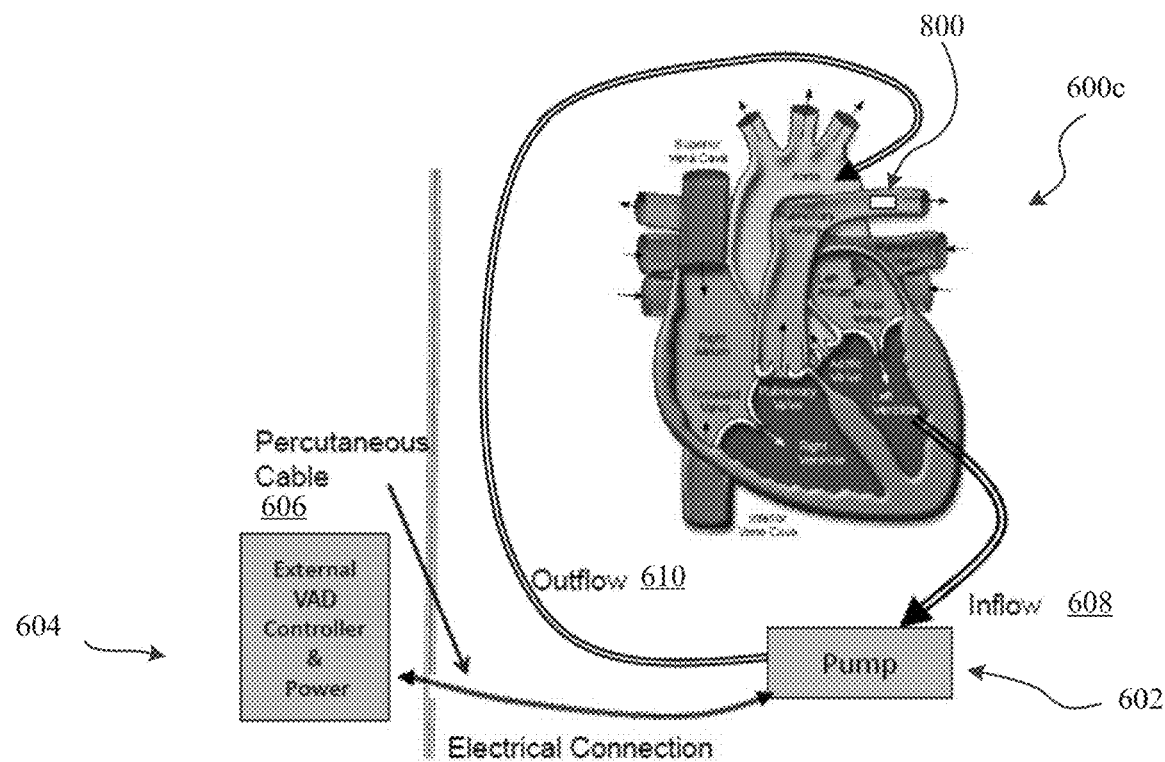
FIG. 9 illustrates another exemplary heart pump system according to some embodiments.

FIG. 9 illustrates another exemplary heart pump system 600c. Heart pump system 600c is similar to the system 600 of FIG. 6 but may further include a pressure sensor 800 that is configured to be implanted within the pulmonary artery of the patient. In some embodiments, the heart pump system 600c does not include pressure sensors integrated with the heart pump 602. The pressure sensor 800, however, may be operably coupled (wired or wirelessly) with pump 602 to transmit pressure measurements from the pulmonary artery. The pump 602 or external controller 604 may analyze the pulmonary arterial pressure waveform and may estimate a left atrial pressure waveform or left ventricular pressure waveform based on the pulmonary arterial pressure waveform. In some embodiments, the ventricular pressure may serve as a proxy for pulmonary arterial pressure.

One or more computing devices may be adapted to provide desired functionality by accessing software instructions rendered in a computer-readable form. When software is used, any suitable programming, scripting, or other type of language or combinations of languages may be used to implement the teachings contained herein. However, software need not be used exclusively, or at all. For example, some embodiments of the methods and systems set forth herein may also be implemented by hard-wired logic or other circuitry, including but not limited to application-specific circuits. Combinations of computer-executed software and hard-wired logic or other circuitry may be suitable as well.

Embodiments of the methods disclosed herein may be executed by one or more suitable computing devices. Such system(s) may comprise one or more computing devices adapted to perform one or more embodiments of the methods disclosed herein. As noted above, such devices may access one or more computer-readable media that embody computer-readable instructions which, when executed by at least one computer, cause the at least one computer to implement one or more embodiments of the methods of the present subject matter. Additionally or alternatively, the computing device(s) may comprise circuitry that renders the device(s) operative to implement one or more of the methods of the present subject matter.

Any suitable computer-readable medium or media may be used to implement or practice the presently-disclosed subject matter, including but not limited to, diskettes, drives, and other magnetic-based storage media, optical storage media, including disks (e.g., CD-ROMS, DVD-ROMS, variants thereof, etc.), flash, RAM, ROM, and other memory devices, and the like.

In the description above, various embodiments of the present invention are described. For purposes of explanation, specific configurations and details are set forth in order to provide a thorough understanding of the embodiments. However, it will also be apparent to one skilled in the art that the present invention may be practiced without the specific details. Furthermore, well-known features may be omitted or simplified in order not to obscure the embodiment being described. The subject matter of the present invention is described here with specificity, but the claimed subject matter may be embodied in other ways, may include different elements or steps, and may be used in conjunction with other existing or future technologies.

This description should not be interpreted as implying any particular order or arrangement among or between various steps or elements except when the order of individual steps or arrangement of elements is explicitly described. Different arrangements of the components depicted in the drawings or described above, as well as components and steps not shown or described are possible. Similarly, some features and sub-combinations are useful and may be employed without reference to other features and sub-combinations. Embodiments of the invention have been described for illustrative and not restrictive purposes, and alternative embodiments will become apparent to readers of this patent. Accordingly, the present invention is not limited to the embodiments described above or depicted in the drawings, and various embodiments and modifications may be made without departing from the scope of the claims below.

Other variations are within the spirit of the present invention. Thus, while the invention is susceptible to various modifications and alternative constructions, certain illustrated embodiments thereof are shown in the drawings and have been described above in detail. It should be understood, however, that there is no intention to limit the invention to the specific form or forms disclosed, but on the contrary, the intention is to cover all modifications, alternative constructions, and equivalents falling within the spirit and scope of the invention, as defined in the appended claims.

The use of the terms "a" and "an" and "the" and similar referents in the context of describing the invention (especially in the context of the following claims) are to be construed to cover both the singular and the plural, unless otherwise indicated herein or clearly contradicted by context. The terms "comprising," "having," "including," and "containing" are to be construed as open-ended terms (i.e., meaning "including, but not limited to,") unless otherwise noted. The term "connected" is to be construed as partly or wholly contained within, attached to, or joined together, even if there is something intervening. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate embodiments of the invention and does not pose a limitation on the scope of the invention unless otherwise claimed. No language in the specification should be construed as indicating any non-claimed element as essential to the practice of the invention.

Preferred embodiments of this invention are described herein, including the best mode known to the inventors for carrying out the invention. Variations of those preferred embodiments may become apparent to those of ordinary skill in the art upon reading the foregoing description. The inventors expect skilled artisans to employ such variations as appropriate, and the inventors intend for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

All references, including publications, patent applications, and patents, cited herein are hereby incorporated by reference to the same extent as if each reference were individually and specifically indicated to be incorporated by reference and were set forth in its entirety herein.

What is claimed is:

1. A blood pump system, the system comprising:
a blood pump comprising an inflow and an outflow,
an upstream pressure sensor coupled with the outflow of the blood pump at an upstream location;
a downstream pressure sensor coupled with the outflow of the blood pump at a downstream location; and
a controller operably coupled with the blood pump, the upstream pressure sensor, and the downstream pressure sensor, the controller configured to:
calibrate measurements from the upstream pressure sensor and the downstream pressure sensor to account for sensor drift;
determine a differential pressure across the blood pump; and
calculate, based on the differential pressure: 1) a pressure at the inflow of the blood pump, or 2) a pressure at the outflow of the blood pump.

2. The blood pump system of claim 1, wherein the controller is further configured to:
generate a desired data waveform based on the calculated pressure; and
output the generated data waveform.

3. The blood pump system of claim 2, wherein the controller is configured to adjust a pumping of the blood pump in response to the generated data waveform.

4. The blood pump system of claim 2, wherein the controller is configured to adjust a pumping mode of the blood pump in response to the generated data waveform.

5. The blood pump system of claim 2, wherein the controller adjusts a pump rotor speed in response to the generated data waveform.

6. The blood pump system of claim 2, wherein the generated data waveform comprises a left ventricular pressure waveform and wherein the left ventricular pressure waveform is calculated by subtracting the differential pressure from the calculated pressure.

7. The blood pump system of claim 1, wherein the upstream pressure sensor is integrated into a housing of the blood pump at the outflow of the blood pump.

8. The blood pump system of claim 1, wherein the upstream pressure sensor is positioned within an outflow graft coupled to the blood pump.

9. The blood pump system of claim 1, wherein the controller determines the differential pressure across the blood pump by accessing a lookup table associating rotor drive current signal values with differential pressure values.

10. The blood pump system of claim 1, further comprising a pulmonary pressure sensor configured to be implanted within a pulmonary artery of a patient, wherein the controller is further configured to:
receive pulmonary pressure measurements from the pulmonary pressure sensor; and
estimate a left atrial pressure waveform or a left ventricular pressure waveform based on the pulmonary pressure measurements.

11. A blood pump system, the system comprising:
a blood pump comprising an inflow and an outflow,
an upstream pressure sensor coupled with the outflow of the blood pump at an upstream location;
a downstream pressure sensor coupled with the outflow of the blood pump at a downstream location; and
a controller operably coupled with the blood pump, the upstream pressure sensor, and the downstream pressure sensor, the controller configured to:
determine a differential pressure across the blood pump based on a rotor drive current signal configured to drive the blood pump; and calculate, based on the differential pressure: 1) a pressure at the inflow of the blood pump, or 2) a pressure at the outflow of the blood pump.

12. The blood pump system of claim 11, wherein the controller is configured to calibrate measurements from the upstream pressure sensor and the downstream pressure sensor to account for sensor drift.

13. A method for hemodynamic monitoring of a patient with a heart pump, the method comprising:
determining a differential pressure across the heart pump having an inflow and an outflow;
receiving an upstream pressure measurement from an upstream pressure sensor coupled with the outflow of the heart pump at an upstream location;
receiving a downstream pressure measurement from a downstream pressure sensor coupled with the outflow of the heart pump at a downstream location;
calibrating measurements from the upstream pressure sensor and the downstream pressure sensor to account for sensor drift; and
generating a desired data waveform based on the differential pressure and at least one of the upstream pressure measurement or the downstream pressure measurement.

14. The method of claim 13, comprising outputting the desired data waveform to a clinician.

15. The method of claim 13, further comprising adjusting a pump operation based on the desired data waveform.

16. The method of claim 13, wherein the heart pump is configured to be coupled with a right ventricle of the patient, and wherein the desired data waveform comprises a right ventricular pressure waveform.

17. The method of claim 13, wherein the heart pump is configured to be coupled with a left atrium of the patient, and wherein the desired data waveform comprises a left atrial pressure waveform.

18. The method of claim 13, wherein the heart pump is configured to be coupled with a left ventricle of the patient, and wherein the desired data waveform comprises a left ventricular pressure waveform.

19. A method for hemodynamic monitoring of a patient with a heart pump, the method comprising:
determining a differential pressure across the heart pump having an inflow and an outflow, wherein the differential pressure is determined based on a rotor drive current signal configured to drive the heart pump;
receiving an upstream pressure measurement from an upstream pressure sensor coupled with the outflow of the heart pump at an upstream location;
receiving a downstream pressure measurement from a downstream pressure sensor coupled with the outflow of the heart pump at a downstream location; and
generating a desired data waveform based on the differential pressure and at least one of the upstream pressure measurement or the downstream pressure measurement.

20. The method of claim 19, further comprising calibrating measurements from the upstream pressure sensor and the downstream pressure sensor to account for sensor drift.

* * * * *